US012755379B2

(12) United States Patent
Orasanu et al.

(10) Patent No.: US 12,755,379 B2
(45) Date of Patent: Oct. 6, 2026

(54) IMAGING WITH ADJUSTABLE ANATOMICAL PLANES

(71) Applicant: KONINKLIJKE PHILIPS N.V., Eindhoven (NL)

(72) Inventors: Eliza Teodora Orasanu, Hamburg (DE); Frank Michael Weber, Norderstedt (DE); Niels Nijhof, Utrecht (NL); Rolf Juergen Weese, Norderstedt (DE); Michel Van Geffen, Eindhoven (NL); Albert Louw Faber, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 286 days.

(21) Appl. No.: 18/567,054

(22) PCT Filed: May 31, 2022

(86) PCT No.: PCT/EP2022/064686
§ 371 (c)(1),
(2) Date: Dec. 5, 2023

(87) PCT Pub. No.: WO2022/258426
PCT Pub. Date: Dec. 15, 2022

(65) Prior Publication Data

US 2024/0265535 A1 Aug. 8, 2024

(30) Foreign Application Priority Data

Jun. 9, 2021 (EP) .................................... 21178479

(51) Int. Cl.
*G06F 3/04815* (2022.01)
*A61B 34/10* (2016.01)
(Continued)

(52) U.S. Cl.
CPC ............ *G06T 7/0012* (2013.01); *A61B 34/10* (2016.02); *A61B 34/20* (2016.02);
(Continued)

(58) Field of Classification Search
CPC ....... A61B 8/523; A61B 8/483; A61B 8/0883; A61B 2034/2065; A61B 2034/105;
(Continued)

(56) References Cited

U.S. PATENT DOCUMENTS

| | | | | |
|---|---|---|---|---|
| 10,339,710 | B2 * | 7/2019 | Holthuizen | G06T 19/003 |
| 2003/0095120 | A1 | 5/2003 | Koppe et al. | |
| 2014/0052001 | A1 * | 2/2014 | Lonasec | A61B 5/7264 600/440 |

FOREIGN PATENT DOCUMENTS

| | | | |
|---|---|---|---|
| EP | 2521098 | A1 | 11/2012 |

OTHER PUBLICATIONS

Faletra et al. "Echocardiographic-fluoroscopic fusion imaging for transcatheter mitral valve repair guidance." Eur Heart J Cardiovasc Imaging. Jul. 1, 2018;19(7):715-726. doi: 10.1093/ehjci/jey067. PMID: 29718146. (Year: 2018).*

(Continued)

*Primary Examiner* — Amandeep Saini
*Assistant Examiner* — Jaspreet Kaur

(57) ABSTRACT

The present invention relates to providing image data of adjustable anatomical planes. In order to provide a more user friendly way of images in selected viewing planes, a device (10) for providing image data of adjustable anatomical planes is provided that comprises a data input (12), a data processor (14), a user interface (16) and an output interface (18). The data input is configured to receive 3D image data of a region of interest of a subject. The data processor is configured to establish anatomical context for identifying anatomical reference locations within the 3D image data.
(Continued)

The data processor is also configured to generate a reference coordinate system based on the identified anatomical reference locations. The data processor is also configured to define an anchor point. The data processor is further configured to compute a viewing plane as a selected anatomical imaging plane based on the anchor point and at least one plane-related parameter. The user interface is configured for entering the at least one plane-related parameter for determining the viewing plane as the selected anatomical imaging plane by the user. The output interface is configured to provide a representation of a view in the selected anatomical imaging plane.

15 Claims, 4 Drawing Sheets

(51) Int. Cl.
*A61B 34/20* (2016.01)
*G06T 7/00* (2017.01)

(52) U.S. Cl.
CPC ... *A61B 2034/102* (2016.02); *A61B 2034/105* (2016.02); *A61B 2034/2065* (2016.02); *G06T 2207/10132* (2013.01)

(58) Field of Classification Search
CPC ... A61B 2034/102; A61B 34/20; A61B 34/10; G06T 19/00; G06T 2219/008; G06T 2210/41; G06T 2200/24; G06T 2207/10132; G06T 7/0012; G06F 3/04845; G06F 3/04815
See application file for complete search history.

(56) References Cited

OTHER PUBLICATIONS

Ecabert et al., “Automatic Model-Based Segmentation of the Heart in CT Images”, IEEE Transactions on Medical Imaging, vol. 27, No. 9, Sep. 2008, pp. 1189-1201.
International Search report and Written Opinion of PCT/EP2022/064686, dated Oct. 18, 2022.

* cited by examiner

IMAGING WITH ADJUSTABLE ANATOMICAL PLANES

CROSS-REFERENCE TO PRIOR APPLICATIONS

This application is the U.S. National Phase application under 35 U.S.C. § 371 of International Application No. PCT/EP2022/064686, filed on May 31, 2022, which claims the benefit of European Patent Application No. 21178479.8, filed on Jun. 9, 2021. These applications are hereby incorporated by reference herein.

FIELD OF THE INVENTION

The present invention relates to a device for providing image data of adjustable anatomical planes, to a system for intervention planning, to a method for providing image data of adjustable anatomical planes as well as to a computer program and a computer readable medium for providing image data of adjustable anatomical planes.

BACKGROUND OF THE INVENTION

As an example, during an intervention on the mitral valve, physicians may use 3D ultrasound to image the structure. In order to understand the anatomy, or in order to estimate relevant anatomical parameters, or in order to plan/guide the intervention, they need to assess the target structure at certain locations. In an example, pre-set view planes are created within the 3D volume in which the relevant information is visible. The manual setting can be a tedious process. In another example, view planes are encoded in a model, and after segmentation, the pre-encoded planes can be retrieved. However, it may be challenging to encode all potentially relevant planes in the model.

SUMMARY OF THE INVENTION

There may thus be a need to provide a more user friendly way of images in selected viewing planes.

The object of the present invention is solved by the subject-matter of the independent claims: further embodiments are incorporated in the dependent claims. It should be noted that the following described aspects of the invention apply also for the device for providing image data of adjustable anatomical planes, for the system for intervention planning and for the method for providing image data of adjustable anatomical planes.

According to the present invention, a device for providing image data of adjustable anatomical viewing planes is provided. The device comprises a data input, a data processor, a user interface and an output interface. The data input is configured to receive 3D image data of a region of interest of a subject. The data processor is configured to establish anatomical context for identifying anatomical reference locations within the 3D image data. The data processor is also configured to generate a reference coordinate system based on the identified anatomical reference locations. The data processor is further configured to define an anchor point. The data processor is still further configured to compute a viewing plane as a selected anatomical imaging plane based on the anchor point and at least one plane-related parameter. The data processor is configured to set the anchor point using the established anatomical knowledge. The user interface is configured for entering the at least one plane-related parameter for determining the viewing plane as the selected anatomical imaging plane by the user. The output interface is configured to provide a representation of a view in the selected anatomical imaging plane.

As an effect, the user is provided with a facilitated and less tedious way of achieving different viewing planes that can be customized for particular needs.

In another claimed option, a device for providing image data of adjustable anatomical viewing planes is provided. The device comprises a data input, a data processor, a user interface and an output interface. The data input is configured to receive 3D image data of a region of interest of a subject. The data processor is configured to establish anatomical context for identifying anatomical reference locations within the 3D image data. The data processor is also configured to generate a reference coordinate system based on the identified anatomical reference locations. The data processor is further configured to define an anchor point. The data processor is still further configured to compute a viewing plane as a selected anatomical imaging plane based on the anchor point and at least one plane-related parameter. The user interface is configured for entering the at least one plane-related parameter for determining the viewing plane as the selected anatomical imaging plane by the user. The output interface is configured to provide a representation of a view in the selected anatomical imaging plane.

According to an example, the output interface comprises a display configured to display the selected plane. As an additional or alternative option, the user interface comprises an adjustment control element configured to adjust the location of the displayed plane. The data processor is configured to provide the adjustment in real-time.

According to an example, the display is configured to display a control image indicating the spatial position of the selected plane within the anatomical context.

According to an example, the anchor point defines the point that will be visible in all possible planes when the user rotates the plane, and, for example, around which the view plane will be rotated.

As an option, provided alternatively or in addition, the at least one plane-related parameter comprises at least one of the group of an angle, a viewing direction, one or more image lines and one or more image points.

According to an aspect, the anchor point is pre-defined, such as the mid-point between antero-lateral and postero-medial commissures. The anchor point is provided for establishing the point around which the (viewing) plane is rotated. In an example, the user shifts the anchor point from the default location along the perpendicular to the AL-PM direction that can be defined by the user. After the anchor point is defined, the user defines an angle. e.g. either by a certain value or with the use of a slider, and this angle is the one that determines the actual plane as the viewing plane. The angle may be provided as a deviation from a perpendicular direction to the AL-PM direction. As an example, an angle which when 0, is the actual perpendicular direction.

According to an example, for establishing anatomical context, the data processor is configured to segment the 3D image data to provide a segmentation of at least a part of the 3D image data. The data processor is also configured to establish anatomical context for identifying the anatomical reference locations within the 3D image data based on the segmentation.

In an option, for segmenting the 3D image data, the data input is configured to receive an anatomical model. The data processor is configured to adapt the model to the 3D image data; and to base the segmenting on the adapted model.

In an additional or alternative option, for establishing anatomical context, the data processor is configured to provide machine learning approaches comprising at least one of the group of machine learning, deep-learning and convolutional neural networks to classify voxels or detect landmarks.

According to an example, the data processor is configured to define the reference system by a first direction along the mitral valve plane normal, a second direction along the antero-lateral and postero-medial direction, and a third direction that is varied accordingly.

In an example, the data processor is configured to apply a user-selected viewing plane for multiple interventions. The multiple interventions can be provided as pre-selected interventions. The interventions can also be referred to as dedicated interventions.

According to the present invention, also a system for intervention planning is provided. The system comprises a device for providing image data of adjustable anatomical viewing planes according to one of the preceding claims. The system also comprises an imaging device for providing images of a region of interest of an object. The imaging device is configured to generate image data of the object und to supply the image data to the device for providing image data of adjustable anatomical planes.

According to an example, the imaging device is an ultrasound imaging device configured to provide 3D ultrasound data.

In an option, the ultrasound imaging device is configured to acquire a 2D ultrasound image according to the selected anatomical imaging plane.

According to the present invention, also a method for providing image data of adjustable anatomical viewing planes is provided. The method comprises the following steps:

- In a first step. 3D image data of a region of interest of a subject is received.
- In a second step, anatomical context for identifying anatomical reference locations within the 3D image data is established.
- In a third step, a reference coordinate system is generated based on the identified anatomical reference locations.
- In a fourth step, an anchor point of a viewing plane is established. The anchor point is set using the established anatomical knowledge.
- In a fifth step, at least one plane-related parameter for determining the viewing plane as a selected anatomical imaging plane is entered by the user.
- In a sixth step, a viewing plane as the selected anatomical imaging plane is computed based on the anchor point and the at least one plane-related parameter.
- In a seventh step, a representation of the selected anatomical imaging plane is provided.

In another claimed option, a method for providing image data of adjustable anatomical viewing planes is provided. The method comprises the following steps: In a first step. 3D image data of a region of interest of a subject is received. In a second step, anatomical context for identifying anatomical reference locations within the 3D image data is established. In a third step, a reference coordinate system is generated based on the identified anatomical reference locations. In a fourth step, an anchor point of a viewing plane is established. In a fifth step, at least one plane-related parameter for determining the viewing plane as a selected anatomical imaging plane is entered by the user. In a sixth step, a viewing plane as the selected anatomical imaging plane is computed based on the anchor point and the at least one plane-related parameter. In a seventh step, a representation of the selected anatomical imaging plane is provided.

According to an example, a pre-set/already defined anchor point is provided. i.e. is available, such as the middle point between the AL and PM, which can be then adjusted/changed along the normal to the AL-PM direction. The pre-set/already defined anchor point may be provided by the system itself of may be adjusted by user entry.

As an example, the anchor point is set by the system. As an option, a location is between the commissures, or at the mitral valve center. In an option, the system sets the anchor point using the anatomical knowledge from the system and knowledge about the intended procedure.

As another example, further adjustments to the anchor point are possible, such as by the system or the user.

After the anchor point has been set, the definition of potential viewing planes is left with one degree of freedom, like the viewing angle. This provides the potential planes, as shown in FIG. 6. Further, to select exactly one of the remaining potential planes, possible inputs are provided, such as: i) numeric angle value, potentially being controlled by a slider, or ii) a point of maximum regurgitant flow, or iii) another anatomical point derived from the model/segmentation, such as an estimate of a location related to different regions of the mitral valve is provided, for example, called A1, A2, A3, P1, P2, P3, or iv) a point clicked by the user on the 3D model.

According to an aspect, imaging with adjustable anatomical planes is provided by establishing a reference system based on anatomical features. By providing one degree of freedom for imaging plane, the user can adapt the viewing plane in an intuitive way and adjust the representation to the current intervention and also to user's needs.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the following drawings.

DETAILED DESCRIPTION OF EMBODIMENTS

Figure 1:
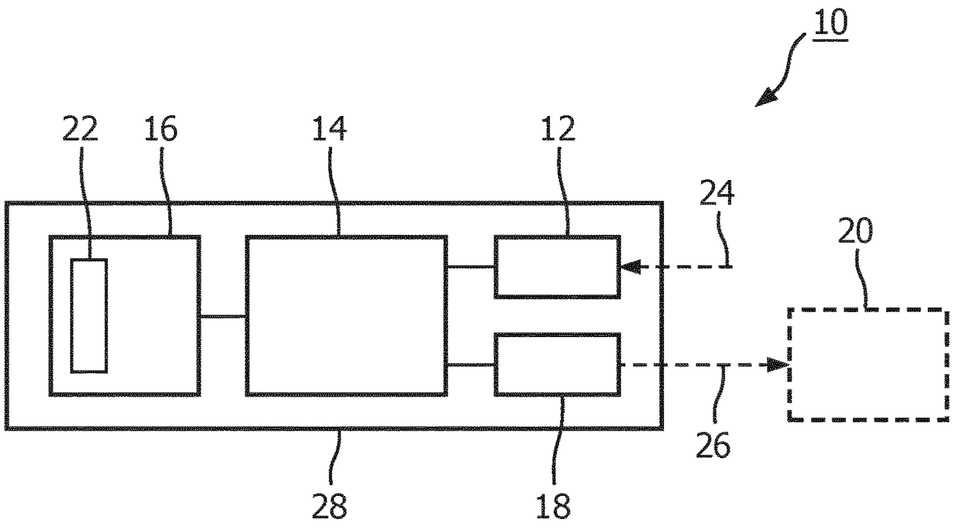
FIG. 1 schematically shows an example of a device for providing image data of adjustable anatomical viewing planes.

Certain embodiments will now be described in greater details with reference to the accompanying drawings. In the following description, like drawing reference numerals are used for like elements, even in different drawings. The matters defined in the description, such as detailed construction and elements, are provided to assist in a comprehensive understanding of the exemplary embodiments. Also, wellknown functions or constructions are not described in detail since they would obscure the embodiments with unnecessary detail. Moreover, expressions such as “at least one of”, when preceding a list of elements, modify the entire list of elements and do not modify the individual elements of the list.

FIG. 1 schematically shows an example of a device 10 for providing image data of adjustable anatomical viewing planes. The device 10 comprises a data input 12, a data processor 14, a user interface 16 and an output interface 18. The data input 12 is configured to receive 3D image data of a region of interest of a subject. The data processor 14 is configured to establish anatomical context for identifying anatomical reference locations within the 3D image data. The data processor 14 is also configured to generate a reference coordinate system based on the identified anatomical reference locations. The data processor 14 is further configured to define an anchor point. The data processor 14 is furthermore configured to compute a viewing plane as a selected anatomical imaging plane based on the anchor point and at least one plane-related parameter. The data processor 14 is configured to set the anchor point using the established anatomical knowledge. The user interface 16 is configured for entering the at least one plane-related parameter for determining the viewing plane as the selected anatomical imaging plane by the user. The output interface 18 is configured to provide a representation of a view in the selected anatomical imaging plane.

A first arrow 24 indicates the input of the 3D image data of a region of interest of a subject. e.g. from a database or from an imaging device. A second arrow 26 indicates the output of the representation of a view in the selected anatomical imaging plane.

A frame 28 indicates that the data input 12, the data processor 14, the user interface 16 and the output interface 18 can be arranged within a common housing or structure. In another option, the data input 12, the data processor 14, the user interface 16 and the output interface 18 are provided as separate components, data-connected with each other.

Figure 2:
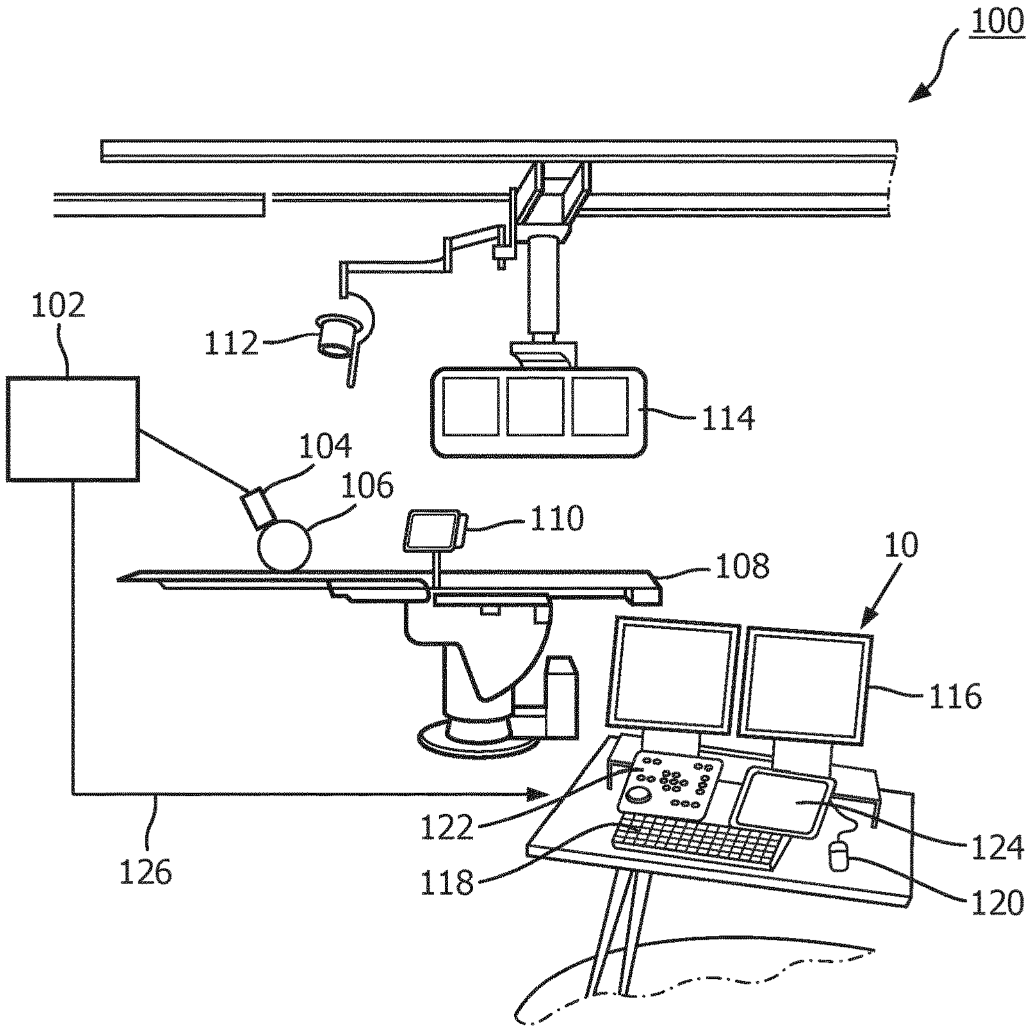
FIG. 2 shows an example of a system for intervention planning with an example of the device for providing image data of adjustable anatomical viewing planes of FIG. 1.

FIG. 2 shows an example of a system 100 for intervention planning. The system 100 comprises an example of the device 10 for providing image data of adjustable anatomical planes of FIG. 1. The system 100 also comprises an imaging device 102 for providing images of a region of interest of an object. The imaging device 102 is configured to generate image data of the object und to supply the image data to the device for providing image data of adjustable anatomical planes.

In an option, the imaging device 102 is an ultrasound imaging device configured to provide 3D ultrasound data. A mobile ultrasound transducer 104 for imaging an object 106 is indicated. Optionally, the ultrasound imaging device is configured to acquire a 2D ultrasound image according to the selected anatomical imaging plane.

FIG. 2 also shows a subject support 108, like a table, with a control panel 110 besides the subject support 108. Further, adjustable lighting equipment 112 is shown as suspended from a ceiling mounted rail structure. Still further a monitor arrangement 114 is also provided suspended from the ceiling mounted rail structure.

The device 10 for providing image data may be provided in the context of an operation console or control arrangement, shown in the right foreground. A display 116 is shown, together with a keyboard 118, a mouse 120, a control panel 122 and graphic tablet 124. The imaging device 102 is data-connected with the device 10 for providing image data of adjustable anatomical planes, as indicated with connecting line 124.

The system 100 for intervention planning can also be referred to as system for intervention guidance.

In an option, not shown, the imaging device is an X-ray imaging device configured to provide 3D X-ray imaging data, such as CT data.

In an option, the acquired 2D view is an additional step once the adapted view plane is provided. The acquired 2D view is so-to-speak in addition to the 2D view in form of the adapted image plane, but the acquired 2D view in better quality.

In another option, the acquired 2D view is provided, once the adapted view plane is defined, but not actually provided. The acquired 2D view is so-to-speak provided as the adapted view plane instead of the 2D view in form of the adapted image plane, but the acquired 2D view is having a better quality as a direct presentation of the adapted image plane would have.

As an aspect. 3D image data. e.g. ultrasound image data, is acquired, and based on the geometrical information, a reformatting is provided within the 3D volume to select and display a selected plane, without any further ultrasound image data acquisition.

In an example, an ultrasound imaging system may provide higher ultrasound image quality in 2D than the image data in 3D. Providing the option to acquire 2D image along the selected and determined viewing plane allows to provide the user, such as physicians, with 2D images with an increased degree of fine details at a specific location (for which the viewing plane has been adapted). Besides the reformatting of the 3D volume, by achieving the defined 2D viewing plane, it is provided to control an ultrasound imaging device to acquire the specific 2D view depending on the current user selection.

In an example, it is provided that the device is configured for the following steps:

First, a 3D volume is acquired and analyzed to provide the reference frame;

Second, a user selects the desired 2D viewing plane orientation.

From that, either: a slide through the acquired 3D volume at that location is shown: or a smaller echo volume is re-acquired covering the selected plane with higher frame rate and/or image quality (assuming the ultrasound probe is still in the same location and the reference frame still matches the anatomy). As an option for the re-acquiring, it is provided the steps of: acquiring the exact plane in 2D mode, if geometrically possible. i.e. if it intersects with the transducer position; acquiring a plane in 2D that is as close as possible to the selected plane at the location of the mitral annulus, for example, a plane defined by the intersection of the selected planed and the mitral annulus plane (defines a line)+the probe position (in combination defines a plane); and acquiring a smaller 3D volume. e.g. a thin slab fully including the selected plane. Because the scanned volume is smaller, the frame rate, for example, can be higher.

In an example, the device 10 for providing image data of adjustable anatomical planes is provided for cardiac interventions, such as valve treatment or replacement procedures.

The data input 12 relates to providing the image data to the processor 14. The image data is thus received from a data supply or data source and forwarded to the data processing. The image data may be provided directly from an imaging device or from a data storage. The data input 12 is also referred to as data image input or image data input unit or data receiving module.

The data processor 14 relates to an arrangement for processing data. i.e. for computing steps to process the data. The data processor 14 is also referred to as processing unit or computing unit or processing module.

The user interface 16 relates to a device for allowing user interaction, such as entering control commands for the data processing. An example of data entry is the entering of the at least one plane-related parameter. Another example of the data entry is the selection or change of the viewing plane or imaging plane. The user interface 16 is also referred to as user interaction unit or user interaction module.

The at least one plane-related parameter comprises at least one of the group of an angle, a viewing direction, one or more image lines and one or more image points.

The output interface 18 relates to providing the computed image plane data, for example for displaying purposes. The output interface 18 is also referred to as processed data supply or output unit or output module.

In a first option, the "representation of a view in the selected anatomical imaging plane" refers to the generation of a 2D image from the 3D image data in the 2D viewing plane.

In a second option, provided in addition or as an alternative, the "representation of a view in the selected anatomical imaging plane" refers to the targeted acquisition of a 2D ultrasound image in the 2D viewing plane.

In an option, the user interface 16 and the output interface 18 are provided in an integrated manner as bi-directional user interface (not shown in detail).

The image data of adjustable anatomical planes can also be referred to as representations of adjustable anatomical planes.

As a result, the present invention thus provides multi-purpose anatomical planes for intervention planning with a single degree-of-freedom. As an effect, during an intervention, the physician can focus on the procedure, since not being forced to deal with multiple measurement systems between interventions which is difficult and prone to errors. The user is thus provided with an option to determine whatever viewing plane is needed, which means a more user-friendly way of providing data than to refine e.g. pre-encoded planes.

To this end, information is extracted from the model for certain relevant structures and the remaining refinement for achieving the most appropriate view is chosen by the user. This can be done for each problem at hand.

In an example, the anchor point of a viewing plane is determined, respectively defined. i.e. the data processor 14 is further configured to determine or define the anchor point.

In an example, a common reference frame and a user interface for multiple mitral valve interventions is provided. From the segmentation, some anatomical constraints are defined.

For example the normal direction of the mitral valve and the anchor point around which planes are rotated are defined.

For example, the center of the mitral valve is defined, and then the anchor point can be defined relative to the center and normal direction of the mitral valve.

With a single control, such as a slider, the user can adjust the plane in a way that it covers a set of anatomically interesting locations. e.g. planes cutting primarily on a direct path from the anterior to the posterior leaflet. Solely by the choice of the anchor point and the plane-related parameter, such as the angle as an option, the method can be applied to interventions that directly target the mitral leaflets, or procedures that target the mitral annulus. In an example, the user interface and the relevant anatomical boundaries are the same for both procedures. For example, the initial position may be a reference view along the AP-direction in the center of the mitral valve, and a certain position of the slider may correspond to a plane that cuts through the commissure points. Furthermore, in an example, external information is included into the same reference frame. i.e. setting the plane to the location of a tracked device, or to the location in which high regurgitant flow has been detected. Such locations can be encoded within the reference coordinate system so that the user controls can be updated and the physician can further navigate from there.

In an example, for the segmentation, the data processor 14 comprises a segmentor, also referred to as segmentation unit. In another example, for the setting up the reference coordinate system, the data processor 14 comprises a geometrical post-processing definer, also referred to as geometrical post-processing unit. The geometrical post-processing definer or geometrical post-processing unit can be provided as separate processor or be integrated in a common processor circuit. In a further example, for the computing of the view plane, the data processor 14 comprises a view plane updater, also referred to as view plane update unit.

In an option, also shown in FIG. 1, the output interface 18 comprises a display 20 configured to display the selected plane.

In another option, also shown in FIG. 1, the user interface 16 comprises an adjustment control element 22 such as a slider or knob, or virtual representation thereof on a touch sensitive display interface, configured to adjust the location of the displayed plane by user interaction.

As an example, the data processor 14 is configured to provide the adjustment in real-time. The term real-time refers to an update within a time span that the user receives as neglectable. e.g. within less than five seconds, such as within less than two or less than one second.

In an example, the user interface 16 comprises a slider element that controls an angle between the central direction between and the displayed plane. The central direction can further be defined as the perpendicular plane to the commissures plane going through the mitral valve center.

In an example, the user interface 16 comprises a slider element that controls an angle of the displayed plane.

If the plane is adjusted by enforcing it to cut through a distinct anatomical point. e.g. a region of high regurgitant flow, this plane position corresponds to an angle in the defined coordinate system, and the slider can be adjusted to that angle position. Then, the user can further manipulate the plane from this position.

In an example, a variable view plane unit is represented by an interface that can take as inputs either an angle value or a point chosen by the user. This will be used to compute the new view plane, and in the case of the latter, the angle from the given point will also be computed and updated. In an example, an interactive component for modifying views is provided.

In an example, the anchor point defines the point that will be visible in all possible planes when the user rotates the plane and around which the rotation is taking place.

For establishing anatomical context, the data processor 14 may be configured to:

segment the 3D image data to provide a segmentation of at least a part of the 3D image data;

establish anatomical context for identifying the anatomical reference locations within the 3D image data based on the segmentation.

Optionally:

i) for segmenting the 3D image data, the data input 12 is configured to receive an anatomical model; and the data processor 14 is configured to adapt the model to the 3D image data and to base the segmenting on the adapted model; and/or ii) for establishing anatomical context, the data processor 14 is configured to provide machine learning approaches comprising at least one of the group of machine learning, deep-learning and convolutional neural networks to classify voxels or detect landmarks.

In the first approach, the model is used for the segmentation of the image data. In an example, the model comprises labels for indicating predefined anatomical features, such as anatomical landmarks. As a result, segmented image data of the patient is provided and, in addition, also geometrical landscape landmarks can be provided.

In the second approach, the knowledge for identifying the anatomical structures within the image data is provided by the machine learning algorithm.

In an example, for the generation of the reference coordinate system, the data processor 14 is configured to provide at least one of the group of:

i) a location of the mitral commissures is provided comprising at least one of the group of antero-lateral mitral commissure and postero-medial mitral commissure;

ii) a direction normal to the mitral valve plane; and iii) a point representing the center of the mitral valve.

In an example, the direction normal to the mitral valve plane is provided roughly normal to the mitral valve plane. As an example, the term roughly relates to a deviation of maximum up to +/−25°. e.g. up to +/−10° or up to +/−5°.

In an example, for determining the direction normal to the mitral valve plane, such as the direction roughly normal, the data processor 14 is configured to determine a regression plane fitting through at least a part of all vertices of the mitral annulus or by taking a cross product between vectors connecting the anterior-posterior end and connection the antero-lateral and postero-medial end of the mitral commissures.

In an example, the data processor 14 is configured to define the reference system by a first direction along the mitral valve plane normal, a second direction along the antero-lateral and postero-medial direction, and a third direction that is varied accordingly.

The antero-lateral and postero-medial direction refers to the direction from the antero-lateral commissure point to the postero-medial commissure point.

The data processor may 14 be configured to use information about locations of actual high regurgitant flow to set the plane location.

As an option, the display 20 is configured to display a control image indicating the spatial position of the selected plane within the anatomical context.

The term spatial position refers to location and orientation in space in relation to the anatomical structure.

The data processor 14 is configured to apply a user-selected viewing plane for multiple interventions.

In an example, the data processor 14 is configured to apply the user-selected viewing plane also for other imaging modalities.

Figure 3:
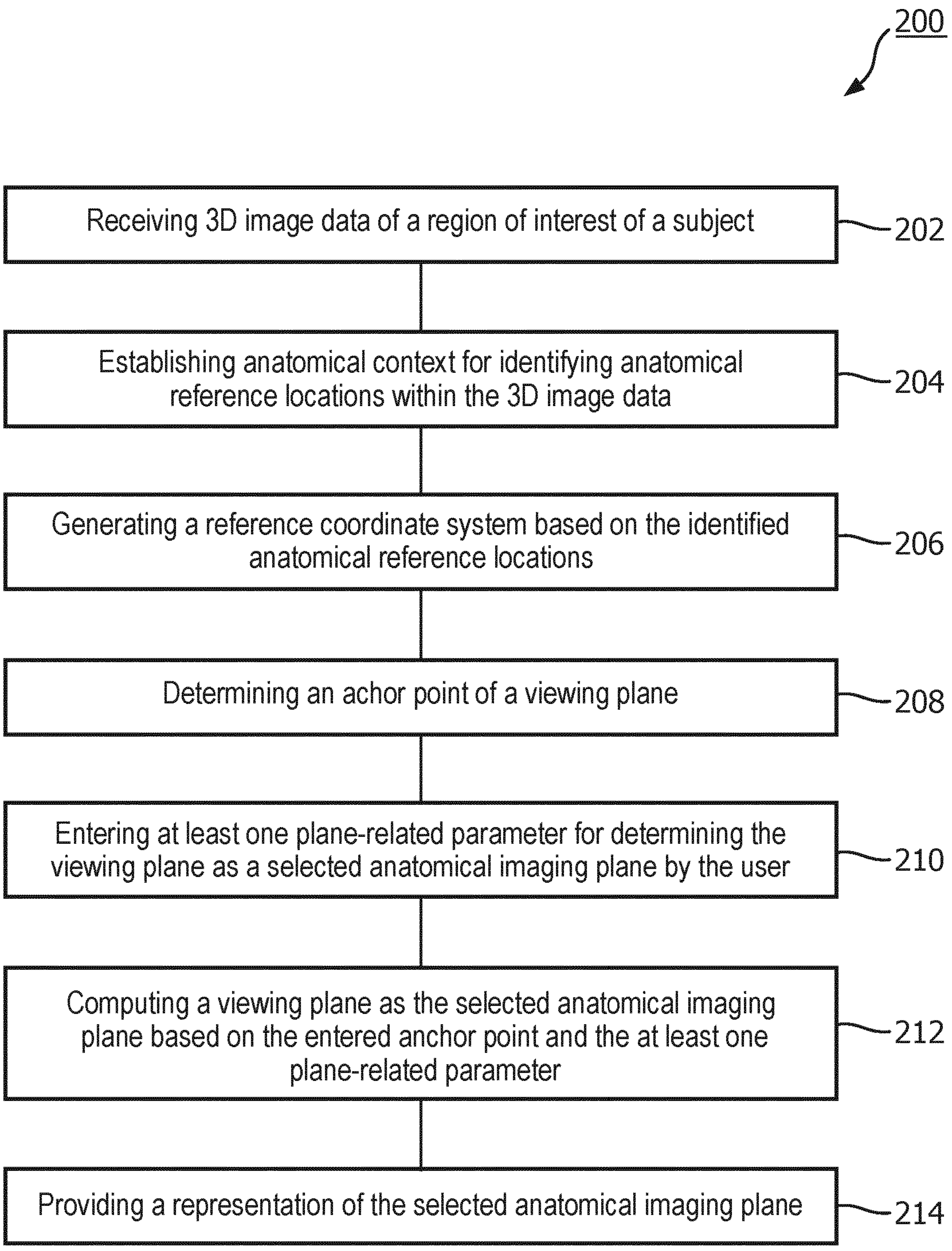
FIG. 3 shows an example of steps of a method for providing image data of adjustable anatomical viewing planes.

FIG. 3 shows an example of steps of a method 200 for providing image data of adjustable anatomical planes. The method comprises the following steps:

In a first step 202, receiving 3D image data of a region of interest of a subject is provided.

In a second step 204, establishment of anatomical context for identifying anatomical reference locations within the 3D image data is provided.

In a third step 206, generation of a reference coordinate system based on the identified anatomical reference locations is provided.

In a fourth step 208, establishing an anchor point of a viewing plane is provided. The anchor point is set using the established anatomical knowledge.

In a fifth step 210, entering at least one plane-related parameter for determining the viewing plane as a selected anatomical imaging plane by the user is provided.

In a sixth step 212, computing a viewing plane as the selected anatomical imaging plane based on the anchor point and the at least one plane-related parameter is provided.

In a seventh step 214, providing a representation of the selected anatomical imaging plane is provided.

The generating of the reference coordinate system is also referred to as setting up a reference coordinate system.

In an example, the anchor point of the viewing plane is determined, respectively defined.

In an example, the anchor point is provided. i.e. determined by the system, as a default option, such as the middle point between the antero-lateral and the postero-medial commissures.

In another example, the anchor point is shifted from the default option along the perpendicular direction to the direction from the antero-lateral commissure point to the postero-medial commissure point by the user for determining the viewing plane as a selected anatomical imaging plane is provided.

In an example, as the at least one plane-related parameter, the user enters a viewing angle. In an example, the user enters a viewing direction, or one or more image lines or one or more image points. For example, the user enters or adapts the viewing angle, or other plane-related parameter, via a slider or via entering a specific value.

In another example, the plane related parameter is an image point. An example of an image point is a point within the 3D image data, Another example of an image point is a point that is determined from the anatomical model, such as an A1 or A2 anatomical point. In an example, an image line is defined by two geometrical points in the image space. In another example, the image content is considered for the image line. e.g. defined by an image gradient.

The anchor point defines the point that will be visible in all possible planes when the user rotates the plane. As also explained below, in an example, the anchor point determines for which procedure the planes are provided. With the selected anchor point being fixed, the user then still has one degree of freedom. e.g. an angle, a clicked point or the location of high regurgitant flow to fully define the plane.

The anchor point can also be referred to as reference position.

In an example of the method, the anchor point, or reference position, for determining a viewing plane can be adjusted by the user.

In an example, the choice of the anchor point is used to determine for which procedure the planes are provided. e.g. cardioband procedures or mitral annulus procedures.

In another example, a shift of the anchor point towards the mitral valve center is allowed, while keeping the same vertical directions in the middle between the projected commissures.

In an example, the anchor point or reference position is varied by an angle or definition of another point instead of the mitral valve center and a new view is then defined.

As an example, the angle is provided. e.g. by a user slider that does not change the anchor point.

In an example, the image data is ultrasound image data.

In an example of the method, for establishing anatomical context, it is provided the step of segmenting the 3D image data providing a segmentation of at least a part of the 3D image data. The establishing anatomical context for identifying the anatomical reference locations within the 3D image data is based on the segmentation.

In an example of the method, for segmenting the 3D image data, an anatomical model is provided. In an option, the model is adapted to the 3D image data. In another option, the segmenting is based on the adapted model.

In an example, after adaptation of the model to the image, anatomical reference locations are extracted from the model. e.g. by looking at which mesh triangles or vertices carry along a certain set of anatomical labels. For example, this can be the location of the mitral annulus, the leaflets, the commissures or the center of the mitral valve.

In an example of the method, for establishing anatomical context, machine learning approaches are provided comprising at least one of the group of deep-learning and convolutional neural networks to classify voxels or detect landmarks.

In an example of the method, for the generation of the reference coordinate system it is provided at least one of the group of:

i) a location of the mitral commissures is provided comprising at least one of the group of antero-lateral mitral commissure and postero-medial mitral commissure;

ii) a direction normal to the mitral valve plane; and iii) a point representing the center of the mitral valve.

In an example of the method, for determining the direction normal to the mitral valve plane, a regression plane is determined fitting through at least a part of all vertices of the mitral annulus or by taking a cross product between vectors connecting the anterior-posterior end and connection the antero-lateral and postero-medial end of the mitral commissures.

In an example, the point representing the center of the mitral valve is provided as the mean of at least a part of all mitral annulus vertices.

In an example of the method, the reference system is defined by a first direction along the mitral valve plane normal, a second direction along the antero-lateral and postero-medial direction, and a third direction that is varied accordingly.

In an example, the third direction is the direction perpendicular to the antero-lateral and postero-medial direction in the plane defined by the mitral valve normal. This third direction is also referred to as the reference direction or the 0°) plane.

In an example of the method, information about locations of actual high regurgitant flow are used to set the plane location.

For example, results from previous evaluation of flow in another tool is used to set the plane location.

In another example, an anatomical point from the segmentation is used to set the plane location. e.g. the center of a scallop of the posterior mitral leaflet, such as “P1”.

As an example, the adapting of viewing planes is provided for products and systems targeting at intervention planning. e.g. for cardiac interventions, like ultrasound applications for cardiac interventions. The adapting of viewing planes may also be implemented within cloud-based services or applications.

In an example, information about the strength of the regurgitant jet at different plane angles is visible inside or in the vicinity of the control slider. For example, the complete slider could have a color-coded shading, and the color could represent a flow quantity (like red for high flow and blue for low flow). In an example, the underlying value is derived as the maximum flow velocity in the plane, or as an integral over the complete regurgitant jet visible in the plane.

In an option, it is provided the step of saving a particular manually selected plane, so that the same view can be investigated in relation with other subjects for consistency and without having to repeat the plane selection step. In an example, the saving of a particular manually selected plane is provided by saving the computed angle and the anchor point.

In a further option, it is provided the step of applying a particular manually selected plane also for other imaging modalities.

Figure 4:
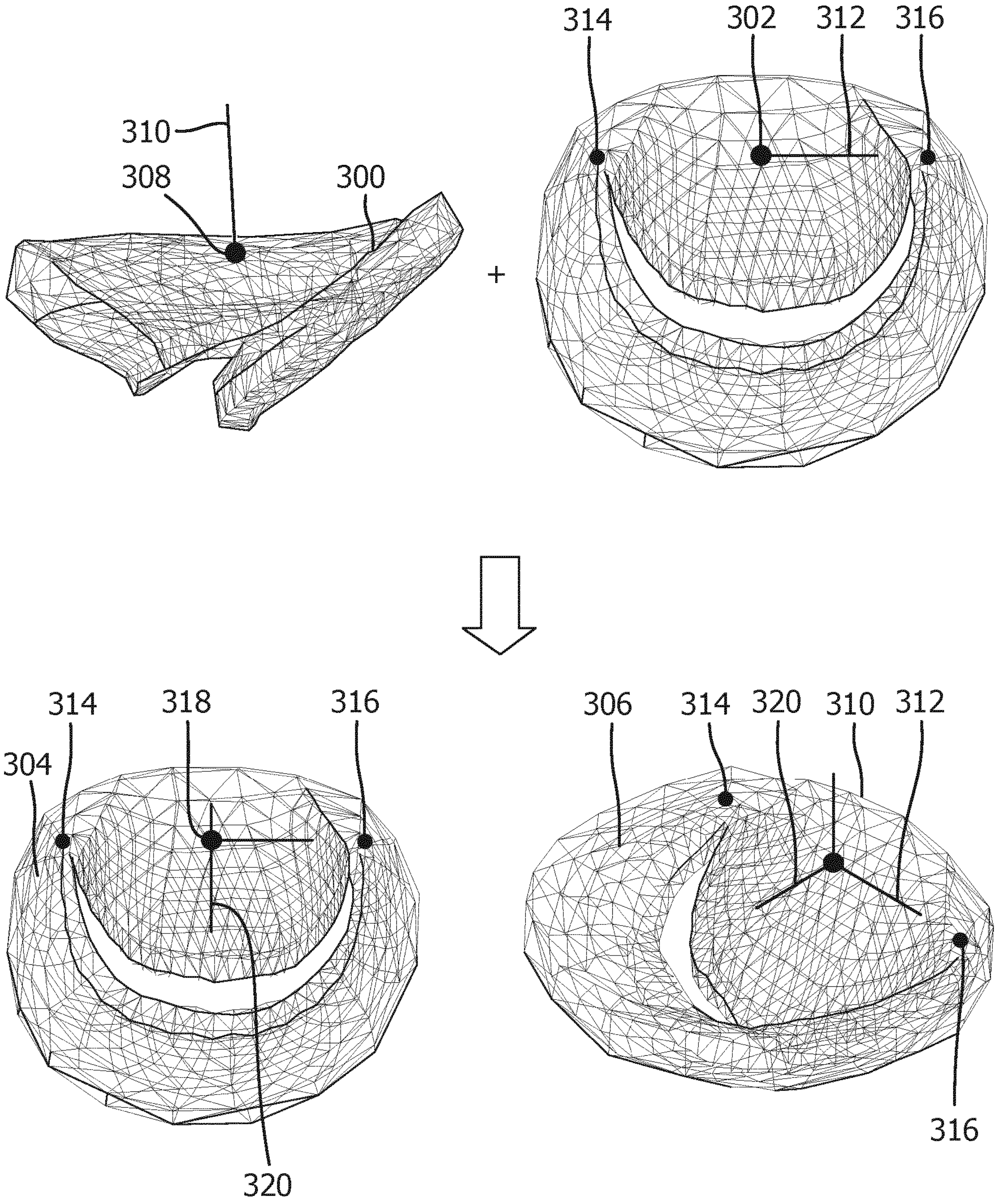
FIG. 4 shows exemplary steps of a procedure of providing image data of adjustable anatomical viewing planes.

FIG. 4 shows exemplary steps of a procedure of providing image data of adjustable anatomical planes. A first representation 300 of an anatomical structure is shown in the top row left. A second representation 302 of the anatomical structure is shown in the top row right, with a different perspective. A third representation 304 of the anatomical structure is shown in the lower row left. A fourth representation 306 of the anatomical structure is shown in the lower row right.

In the top row, a mitral valve center 308 and normal direction 310 to the mitral valve plane in the left part together with a direction 312 from an antero-lateral (AL) mitral commissure 314 to a postero-medial (PM) mitral commissure 316 are indicated.

In the bottom row, a resulting reference system 318 is indicated in the left and right part around which a plane can be defined. The reference system 318 is shown with three different axis. One of the axis, indicated with reference numeral 320, is the reference position used for defining the viewing plane.

Figure 5:
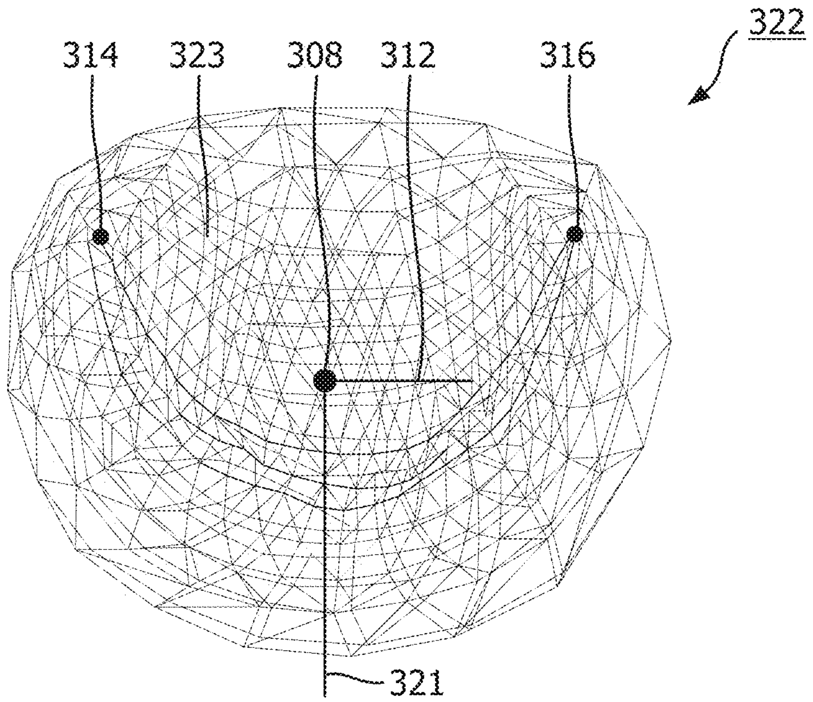
FIG. 5 shows an example of a provided graphical user interface.

FIG. 5 shows an example of a provided graphical user interface 322 showing a fifth representation 323 of the anatomical structure. The antero-lateral mitral commissure 314 is shown as well as the postero-medial mitral commissure 316. Also, the mitral valve center 308 is indicated. FIG. 5 shows a shifted anchor point 321, as a result of user interaction.

It is noted that FIG. 5 is shown also for depicting and explaining the location of the plane. In addition, as indicated, a user interface is provided with the similar appearance.

Figure 6:
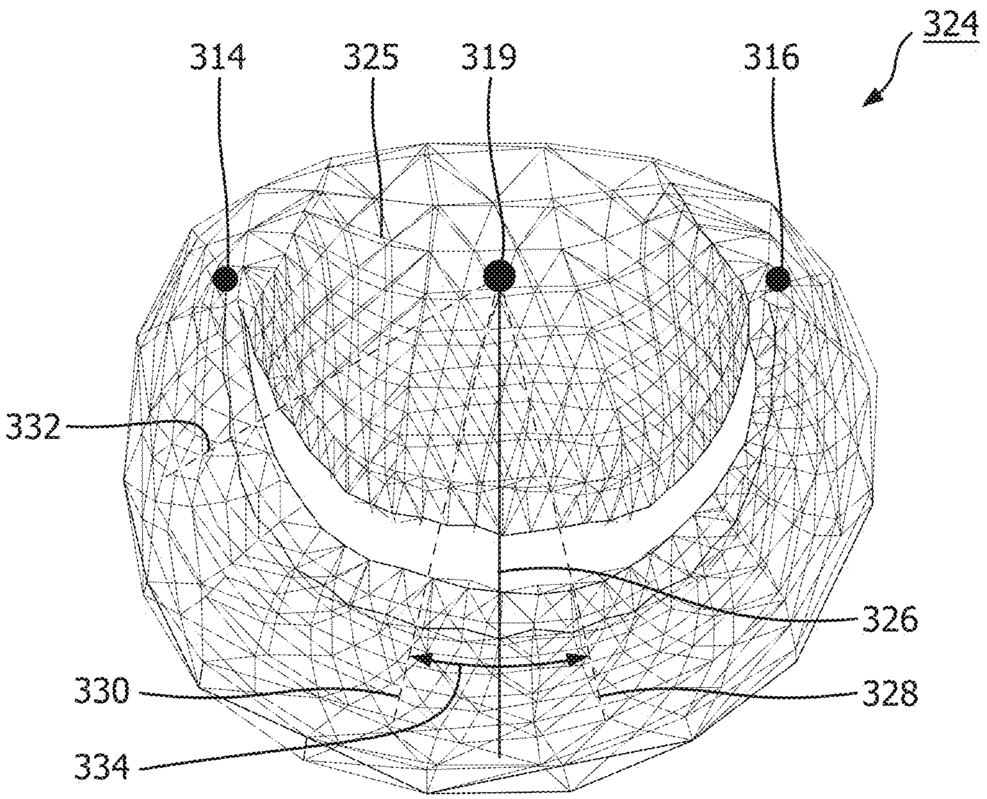
FIG. 6 shows a further example of a provided graphical user interface.

FIG. 6 shows a further example of a graphical user interface 324 showing a sixth representation 325 of the anatomical structure. Again, the antero-lateral mitral commissure 314 is shown as well as the postero-medial mitral commissure 316. Also, the anchor point is indicated with reference numeral 319. The anchor point has been placed between the two commissures. A central line 326 indicates a 0° degree angular line for defining of a variable image plane by the angle. A first line 328 to the right of the central line 326 indicates, as an example, a +10° angular line: a second line 330 to the left of the central line 326 indicates, as an example, a −10° angular line; and a third line 332 indicates, as an example, a −70° angular line. A double arrow 334 indicates an adjustment option for the viewing plane by varying the angular parameter.

The term "subject" may also be referred to as individual. The "subject" may further also be referred to as patient, although it is noted that this term does not indicate whether any illness or disease is actually present with the subject.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit or be distributed over more than one computer units, which might also be part of an embodiment of the present invention. This computing unit may be adapted to perform or induce a performing of the steps 10) of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

Aspects of the invention may be implemented in a computer program product, which may be a collection of computer program instructions stored on a computer readable storage device which may be executed by a computer. The instructions of the present invention may be in any interpretable or executable code mechanism, including but not limited to scripts, interpretable programs, dynamic link libraries (DLLs) or Java classes. The instructions can be provided as complete executable programs, partial executable programs, as modifications to existing programs 20) (e.g. updates) or extensions for existing programs (e.g. plugins). Moreover, parts of the processing of the present invention may be distributed over multiple computers or processors.

As discussed above, the processing unit, for instance a controller implements the control method. The controller can be implemented in numerous ways, with software and/or hardware, to perform the various functions required. A processor is one example of a controller which employs one or more microprocessors that may be programmed using software (e.g., microcode) to perform the required functions. A controller may however be implemented with or without employing a processor, and also may be implemented as a combination of dedicated hardware to perform some functions and a processor (e.g., one or more programmed microprocessors and associated circuitry) to perform other functions.

Examples of controller components that may be employed in various embodiments of the present disclosure include, but are not limited to, conventional microprocessors, application specific integrated circuits (ASICs), and field-programmable gate arrays (FPGAs).

This exemplary embodiment of the invention covers both, a computer program that right from the beginning uses the invention and a computer program that by means of an update turns an existing program into a program that uses the invention.

Further on, the computer program element might be able to provide all necessary steps to fulfil the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section. A computer program may be stored and/or distributed on a suitable medium, such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated, and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A device for providing image data of adjustable anatomical planes of a mitral valve having an antero-lateral (AL) mitral commissure and a postero-medial (PM) mitral commissure, comprising:

- a data input;
- a data processor;
- a user interface; and
- an output interface;
- wherein the data input is configured to receive 3D image data of a region of interest of a subject comprising the mitral valve;
- wherein the data processor is configured to:
  - establish anatomical context for identifying anatomical reference locations within the 3D image data;
  - generate a reference coordinate system based on the identified anatomical reference locations;
  - define an anchor point as the origin of the reference coordinate system, wherein the anchor point is predefined at a location between the antero-lateral and postero-medial commissures; and compute a viewing plane as a selected anatomical imaging plane passing by the anchor point and based on at least one plane-related parameter;

wherein the user interface is configured for entering the at least one plane-related parameter for determining the viewing plane as the selected anatomical imaging plane by a user; and wherein the output interface is configured to provide a representation of a view in the selected anatomical imaging plane.

2. The device according to claim 1, wherein the user interface is configured for entering user entry to adjust the anchor point.

3. The device according to claim 1, wherein the output interface comprises a display configured to display the selected anatomical imaging plane; and/or wherein the user interface comprises an adjustment control element configured to adjust an orientation of the displayed plane; and wherein the data processor is configured to provide the adjustment in real-time.

4. The device according to claim 3, wherein the display is configured to display a control image indicating a spatial position of the selected anatomical imaging plane within the anatomical context.

5. The device according to claim 1, wherein the anchor point defines the point that will be visible in all planes when the user rotates the plane; and/or wherein the at least one plane-related parameter comprises at least one of the group of an angle, a viewing direction, one or more image lines and one or more image points.

6. The device according to claim 1, wherein, for the establishing of the anatomical context, the data processor is configured to:

segment the 3D image data to provide a segmentation of at least a part of the 3D image data;

wherein the establishing of the anatomical context for identifying the anatomical reference locations within the 3D image data is based on the segmentation; and wherein:

i) for segmenting the 3D image data, the data input is configured to receive an anatomical model, and the data processor is configured to:

adapt the anatomical model to the 3D image data; and base the segmenting on the adapted model; and/or ii) for the establishing of the anatomical context, the data processor is configured to provide machine learning approaches comprising at least one of a group of machine learning, deep-learning, and convolutional neural networks to classify voxels or detect landmarks.

7. The device according to claim 1, wherein, for the generation of the reference coordinate system, the data processor is configured to provide at least one of a group of:

i) a location of the mitral commissures is provided comprising at least one of the group of antero-lateral mitral commissure and postero-medial mitral commissure;

ii) a direction normal to a mitral valve plane; and iii) a point representing the center of the mitral valve.

8. The device according to claim 7, wherein, the data processor configured to provide the direction normal to the mitral valve plane is configured to determine a regression plane fitting through at least a part of all vertices of the mitral annulus or by taking a cross product between vectors connecting the anterior-posterior end and connection the antero-lateral and posteromedial end of the mitral commissures.

9. The device according to claim 1, wherein the data processor is configured to define the reference coordinate system by a first direction along the mitral valve plane normal, a second direction along a antero-lateral and postero-medial direction, and a third direction that is varied accordingly.

10. The device according to claim 1, wherein the data processor is configured to use information about locations of actual high regurgitant flow to set a plane location.

11. The device according to claim 1, further comprising an imaging device for providing images of the region of interest of the subject;

wherein the imaging device is configured to generate image data to supply the image data to the data input.

12. The device according to claim 11, wherein the imaging device is an ultrasound imaging device configured to provide 3D ultrasound data such that the 3D image data is the 3D ultrasound data; and wherein the ultrasound imaging device is configured to acquire a 2D ultrasound image according to the selected anatomical imaging plane.

13. A method for providing image data of adjustable anatomical planes of a mitral valve having an antero-lateral (AL) mitral commissure and a postero-medial (PM) mitral commissure, comprising the following steps:

receiving 3D image data of a region of interest comprising the mitral valve of a subject;

establishing anatomical context for identifying anatomical reference locations within the 3D image data;

generating a reference coordinate system based on the identified anatomical reference locations;

establishing an anchor point of a viewing plane as the origin of the reference coordinate system, wherein the anchor point is pre-defined at a location between the antero-lateral and postero-medial commissures;

entering at least one plane-related parameter for determining the viewing plane as a selected anatomical imaging plane by a user;

computing a viewing plane as the selected anatomical imaging plane passing by the anchor point and based on the at least one plane-related parameter; and providing a representation of the selected anatomical imaging plane.

14. A system configured to provide image data of adjustable anatomical planes of a mitral valve having an antero-lateral (AL) mitral commissure and a postero-medial (PM) mitral commissure, the system comprising:

one or more processor configured by machine-readable instructions to:

receive 3D image data of a region of interest comprising the mitral valve of a subject;

establish anatomical context for identifying anatomical reference locations within the 3D image data;

generate a reference coordinate system based on the identified anatomical reference locations;

establish an anchor point of a viewing plane as the origin of the reference coordinate system, wherein the anchor point is pre-defined at a location between the antero-lateral and posteromedial commissures;

enter at least one plane-related parameter for determining the viewing plane as a selected anatomical imaging plane by a user;

compute a viewing plane as the selected anatomical imaging plane passing by the anchor point and based on the at least one plane-related parameter; and provide a representation of the selected anatomical imaging plane.

15. The system of claim 14, further comprising: a computer readable medium that stores the machine-readable instructions.

* * * * *